(12) United States Patent
Gloeckner

(10) Patent No.: US 8,040,499 B2
(45) Date of Patent: Oct. 18, 2011

(54) TRANSMITTED LIGHT REFRACTOMETER

(75) Inventor: Andreas Gloeckner, Berlin (DE)

(73) Assignee: Flexim Flexible Industriemesstechnik GmbH, Berlin (DE)

( * ) Notice: Subject to any disclaimer, the term of this patent is extended or adjusted under 35 U.S.C. 154(b) by 270 days.

(21) Appl. No.: 12/290,038

(22) Filed: Oct. 23, 2008

(65) Prior Publication Data

US 2009/0103076 A1    Apr. 23, 2009

(51) Int. Cl.
*G01N 21/41* (2006.01)
(52) U.S. Cl. .................... 356/137; 356/135; 356/136
(58) Field of Classification Search .................. None
See application file for complete search history.

(56) References Cited

U.S. PATENT DOCUMENTS

| | | | |
|---|---|---|---|
| 3,449,051 A | 6/1969 | Levitt | |
| 3,628,867 A | 12/1971 | Brady | |
| 4,571,075 A | 2/1986 | Kamrat | |
| 5,110,205 A * | 5/1992 | Suzuki et al. | 356/135 |
| 5,347,358 A * | 9/1994 | Nebe et al. | 356/128 |
| 6,067,151 A | 5/2000 | Salo | |
| 7,061,597 B2 * | 6/2006 | Oberleitner et al. | 356/135 |

FOREIGN PATENT DOCUMENTS

| | | |
|---|---|---|
| DE | 30 28 564 | 2/1981 |
| DE | 40 38 123 | 6/1991 |

* cited by examiner

*Primary Examiner* — Gregory J Toatley
*Assistant Examiner* — Amanda H Merlino
(74) *Attorney, Agent, or Firm* — Jordan and Hamburg LLP

(57) ABSTRACT

A transmitted light refractometer allows high measurement accuracy across a broad measurement range, even under difficult measuring conditions. The transmitted light refractometer can be connected to a process simply via a single access. In accordance with advantageous features, the transmitted light refractometer covers a measurement range for all practically relevant media and includes integrated temperature compensation. A reversing optics unit is arranged relative to an illumination optics unit such that the reversing optics unit deflects a parallel beam through the process liquid and a measurement prism into the transmitted light refractometer back to the side from which it was radiated. The illumination optics unit, an imaging optics unit, and a detector plane are arranged on the light radiation side such that only one process access is needed.

10 Claims, 4 Drawing Sheets

TRANSMITTED LIGHT REFRACTOMETER

BACKGROUND OF THE INVENTION

The invention relates to a transmitted light refractometer that works according to the principle of a transmitted light refractometer. A light source illuminates a slit. Using optical components, the emitted light is directed as a beam and enters the process medium through a window. The light passes through the process medium as a parallel beam. The light refraction that is relevant for the measurement occurs when the light re-enters the refractometer through the measurement prism. Optical components produce an image of the slit on the light-sensitive position detector. The light refraction of the process medium is determined from the position determined for the slit image.

The working principle for refractometers has been known for more than one hundred years. In addition to various laboratory tasks, refractometers are increasingly employed in industry. Refractometers are used in the chemical, pharmaceutical, and foods industries for process control and/or online analysis.

In the past, critical angle refractometers have been used in process instrumentation (U.S. Pat. No. 3,628,867 A). These instruments use the principle of total reflection. An optical window is used to tie it to the process, e.g. U.S. Pat. No. 4,571,075 A. The light refraction relevant for the measurement occurs at the interface between the window (greater refractive index) and the process medium (lower refractive index). According to the critical angle principle, a beam strikes the interface with the greatest possible angular distribution. The part of the light having smaller angles of incidence is refracted in the process medium, while light having larger angles of incidence is increasingly totally reflected. A progression from light to dark is measured in the image plane. The refractive index of the process medium is determined using comparatively complex image analysis. In these refractometers, the practical access to the process on one side is advantageous and makes it possible to use them at various measuring points in pipes and tanks.

A broad and uniformly distributed angular spectrum for the light incident on the prism is required for covering the largest possible measuring area with high accuracy. Producing and imaging light with a broad and uniformly distributed angular spectrum is relatively difficult. In order to attain appropriate accuracy for the process, the possible measuring area is therefore generally limited. Therefore it may be necessary to combine a plurality of devices in order to cover the complete measuring area that is required from the process aspect.

The critical angle principle is susceptible to fouling. The interface between process window and process medium that is critical for the measuring effect can become fouled during the process and this fouling can stay undetected because the light is totally reflected at the interface. Regular cleaning and maintenance is necessary to prevent this.

Since critical angle refractometers usually evaluate the light/dark limit of the transition to total reflection, even minor shifts in the overall image on the detector lead to inaccuracy in determining the refractive index. Such shifts are caused for instance by changes in pressure and temperature on the sensor head. Special solutions attempt to render the optical arrangement more robust with respect to external influences (U.S. Pat. No. 6,067,151 A).

Overall, the aforesaid demanding process conditions for critical angle refractometers frequently lead to unintended drift effects in the measured value so that it is not possible to reliably accomplish the process objectives.

The principle of transmitted light refractometers is also known (see FIG. 1). In a transmitted light refractometer, the deflection of a parallel light beam that strikes the interface between the liquid 4 to be measured and the measurement prism 6 is measured, the light passing completely through the liquid in the measuring chamber 5. A slit 1 is illuminated by a light source. A beam is guided using optical components 2 and as a parallel beam 8 enters the process liquid from the interior of the refractometer via an optical window 3. The light passes through the process liquid and again strikes an optical component that forms the transition to the interior of the refractometer. This optical component is called the measurement prism 6. The parallel beam strikes the inclined interface and is refracted there. The deflection of the light beam is a function of the refractive index of the process liquid. Then the parallel beam is focussed onto the detector 9 using an optical component 7.

In a transmitted light refractometer, a sharp image of the slit occurs on the image plane of the detector. The detector is a light-sensitive position detector. The position of the slit image is determined by signal analysis. It is relatively simple to determine the angle of refraction and thus the refractive index of the process liquid from the position.

$$\text{gamma} = \text{ArcSin}((n0/n\text{Ref})\text{Sin}(\text{ArcTan}(x/f))) \qquad (I).$$

Gamma is the angle of deflection after the light exits from the measurement prism.
nRef is the optical refractive index of the measurement prism.
x is the position of the slit image on the detector.
f is the focal length from the imaging optics unit to the detector.
n0 is the optical refractive index of air.

$$\text{beta} = \text{alpha gamma} \qquad (II).$$

Alpha is the angle of incidence of the measurement prism.
Beta is the angle of the refracted light beam in the measurement prism.

$$nD = n\text{Ref}*\text{Sin(beta)}/\text{Sin(alpha)} \qquad (III)$$

nD is the optical refractive index of the process medium.

The parameter x is measured, and the sought variable, nD, can be calculated from it when the device-related variables nRef, alpha, and f are known and when n0 is known.

Transmitted light refractometers are characterized by high measurement accuracy. Determining the position of a sharp image, e.g., of a thin slit, is relatively simple and is even possible without modern electronics. The precision and reliability of the position determined for the slit image can be further enhanced using modern signal processing methods. The angle of deflection, which is a function of the refractive index, can be determined very precisely, and thus the refractive index of the process medium can be measured with great accuracy.

Transmitted light refractometers require that light passes through the entire measurement chamber. This necessitates process access on two-sides if, as is usual, the light source and detector are arranged along one optical axis. In the process, a complex solution that has been structurally specially adapted to the process conditions must be found for each measuring location, so that installation is relatively complex. The aforesaid solution is only practical for smaller process tubes or laboratory applications; measurements in large vessels are not possible.

There are refractometers that evaluate images from two or more beams. These refractometers are called differential refractometers and can be created both as transmitted light refractometers (DE 4038123 A1) and in the form of critical angle refractometers (U.S. Pat. No. 3,449,051 A). The light emitted is divided into two beams that pass through the refractometer on different light paths. One beam travels a light path in which the light is diffracted at a reference liquid. This beam is called the reference beam. The other beam is refracted at the sample and is called the probe beam. The difference between the two images is evaluated in the detector.

Like mass density, optical refraction is a typical material parameter like, for example, density. Other material characteristics such as, for example, the mass concentration of the components in substance mixtures, can be derived from the measured refractive index. These derived variables are frequently the variables that are actually of interest in process instrumentation. Since the refractive index is also a function of media temperature, in general it is not possible to calculate the derived material variables unless the temperature is known (temperature compensation). There are different solutions for compensating the temperature correlation. In the case of critical angle refractometers, during the process temperature detectors are frequently built into the interior of the probe so that the temperature correlation can be corrected afterwards. These internal temperature detectors often do not satisfy the desired demands in terms of reaction time.

Without this additional temperature detector, the differential measuring principle can be used in a special embodiment for temperature compensation such as e.g. DE 3028564 A1. The reference liquid is selected such that its temperature behavior in terms of the refractive index is consistent with the behavior of the sample.

Thus, the measurement is temperature compensated. In this method the lack of flexibility and the structure, which is not appropriate for the process, are disadvantages. In addition, reference liquid and sample liquid frequently have only similar temperature behaviors, but not sufficiently identical temperature behaviors.

The underlying object of the invention is therefore to create a transmitted light refractometer that:

has high measurement accuracy across a broad measurement range, even under difficult measuring conditions;

can be connected to the process simply via a single access;

with a one device embodiment covers a measurement range for all practically relevant media; and, has integrated temperature compensation.

SUMMARY OF THE INVENTION

This object is attained in accordance with the invention using the transmitted light refractometer described in the following. To this end, a reversing optics unit is arranged relative to an illumination optics unit such that the former deflects the parallel beam through the process liquid and a measurement prism into the transmitted light refractometer back to the side from which it was radiated. The illumination optics unit, an imaging optics unit, and a detector plane are arranged on the light radiation side such that only one process access is needed.

The inventive transmitted light refractometer has an optical beam guidance unit that requires access to the process medium on only one side. The parallel beam produced by the light source is thus deflected such that it emerges from an optical window, passes through the process liquid, and through a measurement prism re-enters the transmitted light refractometer on the side from which it was radiated. Because of the novel beam path the structure of the inventive transmitted light refractometer is very compact.

Using special embodiments with a measurement prism as a double prism, high measurement accuracy is attained across a wide range of refractive indices, even given difficult process conditions.

In one embodiment, the illumination optics unit and the imaging optics unit are integrated into the side of the window and measurement prism that faces away from the process.

A temperature detector is arranged in the process liquid, such that it is disposed a short locational distance from the optical measurement segment. To this end, the temperature detector is integrated in a separate, free-standing thin-walled housing part.

Using the invention, the advantages of the critical angle refractometer are combined with principle-based advantages of a transmitted light refractometer.

The invention is explained in greater detail in the following using exemplary embodiments.

DETAILED DESCRIPTION OF THE INVENTION

Figure 1:
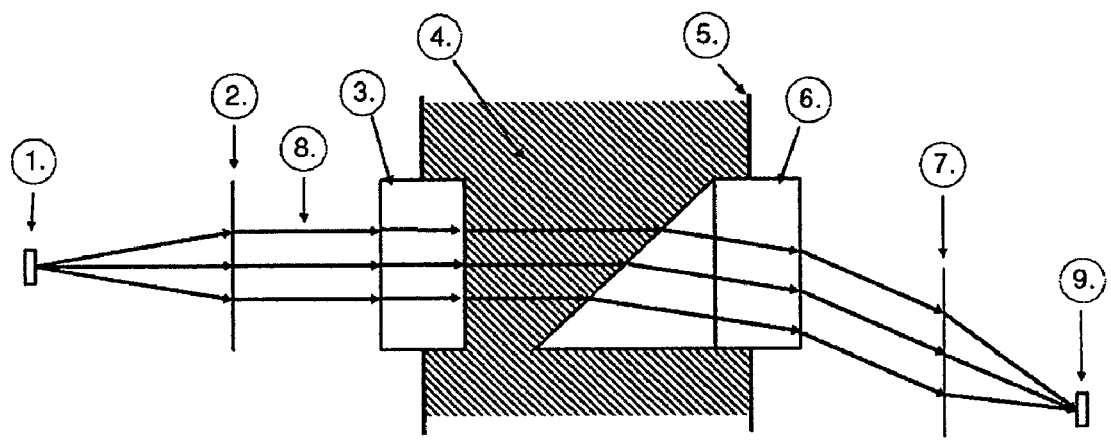
FIG. 1 depicts the principle of a transmitted light refractometer.

FIG. 1 is a diagram of a refractometer from the prior art that is based on the transmitted light principle. Light is emitted from a light source and illuminates a slit 1. The slit 1 is imaged by means of an illumination optics unit 2, preferably a lens. The illumination optics unit parallelizes the beam 8 before it passes through the process medium 4. The light enters the process medium 4 perpendicular thereto via a window 3. The light diffraction relevant to the refractive index measurement occurs at the interface between process medium and measurement prism 6. A sharp image of the slit is produced in the detector plane 9 by the focusing optics unit 7. The angle of refraction and thus the refractive index of the process liquid can be determined from the location of the slit image using formulas I through III.

Figure 2:
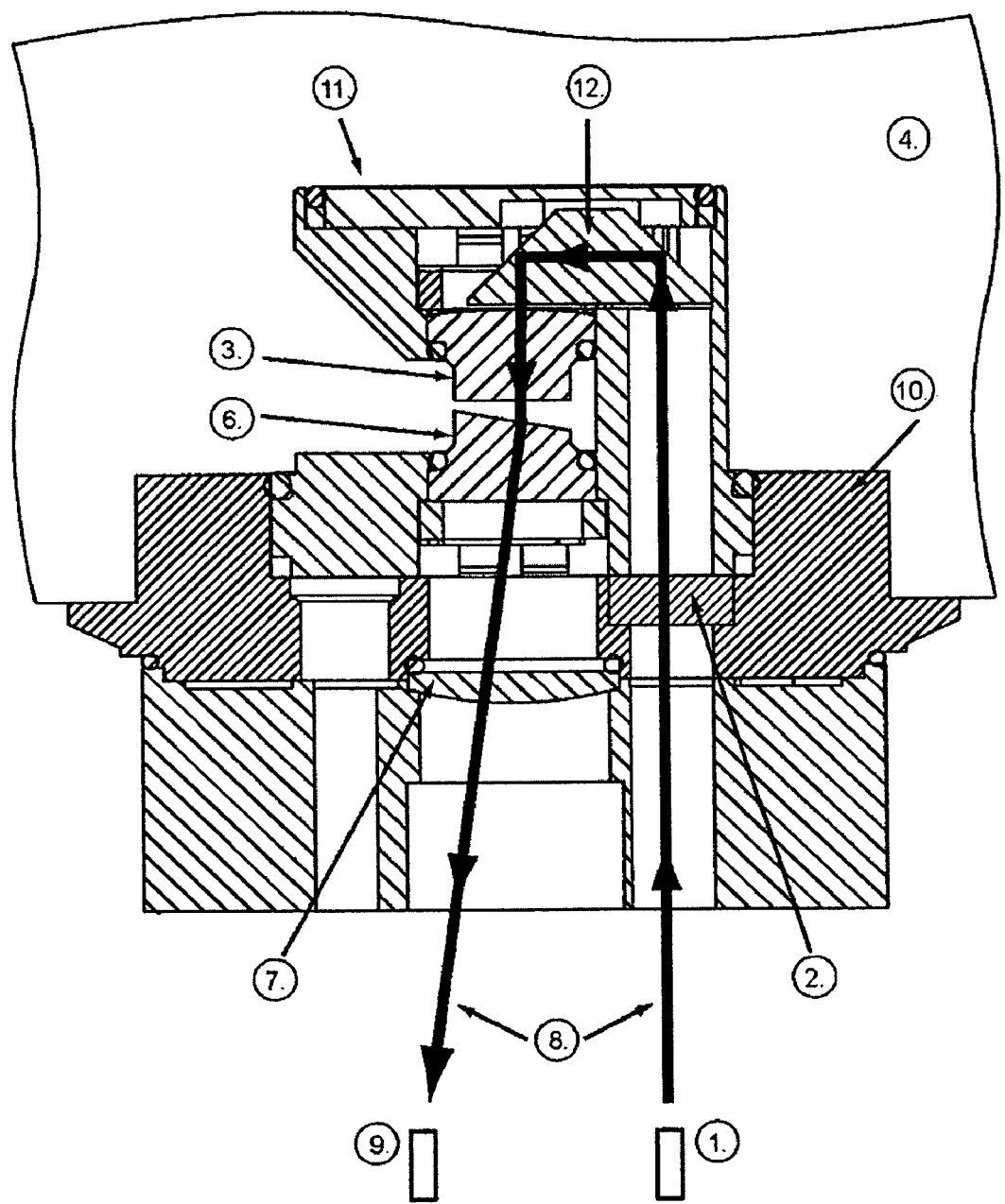
FIG. 2 is a diagram of the transmitted light refractometer in accordance with the invention, with the beam path.

FIG. 2 depicts one embodiment of the inventive transmitted light refractometer. This refractometer works using the transmitted light principle in accordance with FIG. 1, and offers the advantage of access to the process medium 4 from one side. The refractometer is connected to the process via a suitable flange connection 10. The sensor head 11 is disposed in the process medium. Moreover, the transmitted light refractometer in FIG. 2 contains all of the important components from FIG. 1. An LED that illuminates a slit 1 is preferably used for producing the light. The light emitted is parallelized via an illumination lens 2. The illumination and the detector are disposed on the same side of the process container. The direction of propagation of the light is reversed in the sensor head in order to make it possible for the light to pass through the medium without an additional access to the process. The beam reversal can be attained with optical components such as e.g. mirrors. Preferably a dove prism is used as the deflecting optics unit 12, as depicted in FIG. 2. Thus reliable beam reversal is possible with only one optical component. The transmitted light refractometer in accordance with FIG. 2 is very compact and is simple to install in all types of containers such as e.g. pipes and tanks.

In another embodiment of the process refractometer in accordance with FIG. 2, the optical components that come into contact with the measurement medium are preferably made of sapphire. This material is characterized by particularly high mechanical and chemical strength and a particularly high refractive index. With sapphire as the measurement prism material, the inventive embodiment covers a very broad measuring range so that all practically relevant media can be measured with great accuracy. Another embodiment in accordance with FIG. 2 uses a double prism for the measurement prism.

Figure 3:
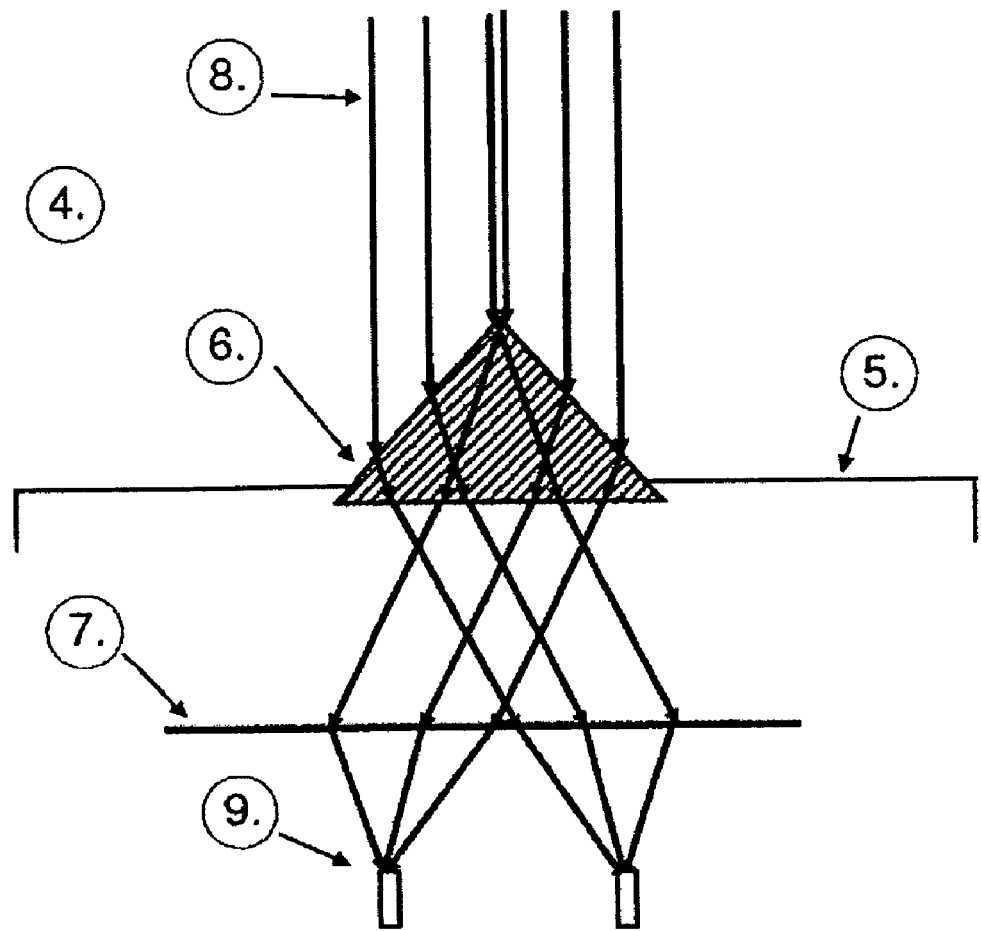
FIG. 3 is an optical diagram of a double prism.

FIG. 3 diagrams the optics for the embodiment having a double prism. A parallel beam 8 is incident on a measurement prism 6 that is embodied as a double prism. It has two inclined planar surfaces that are symmetrical with a plane of symmetry, the symmetry surface being perpendicular to the reference plane.

The two inclined planar surfaces form the interfaces to the process medium. The light refraction that is relevant for measuring the refractive index occurs at these interfaces to the process medium 4. At the same time this prism acts as a beam splitter so that using the focussing optics unit 7 two images of the slit occur in the detector plane 9.

Independent of one another, the beams from the two slit images have passed through all of the optical components and the measurement medium and contribute to measuring the refractive index so that both beams can be called probe beams.

The angle of deflection and thus the refractive index of the process medium can be determined, independent of one another, both from the absolute locational position of the two slit images and from the relative locational position of the two slit images relative to one another. The relative locational measurement has the particular advantage that it is unrelated to the external process conditions such as, for example, pressure and temperature, since these influences occur in equal measure and negate one another in the evaluation. This arrangement is particularly suitable for providing drift-free and reliable measurements given difficult process conditions, in particular highly changeable process conditions, such as high temperature and pressure gradients.

Figure 4:
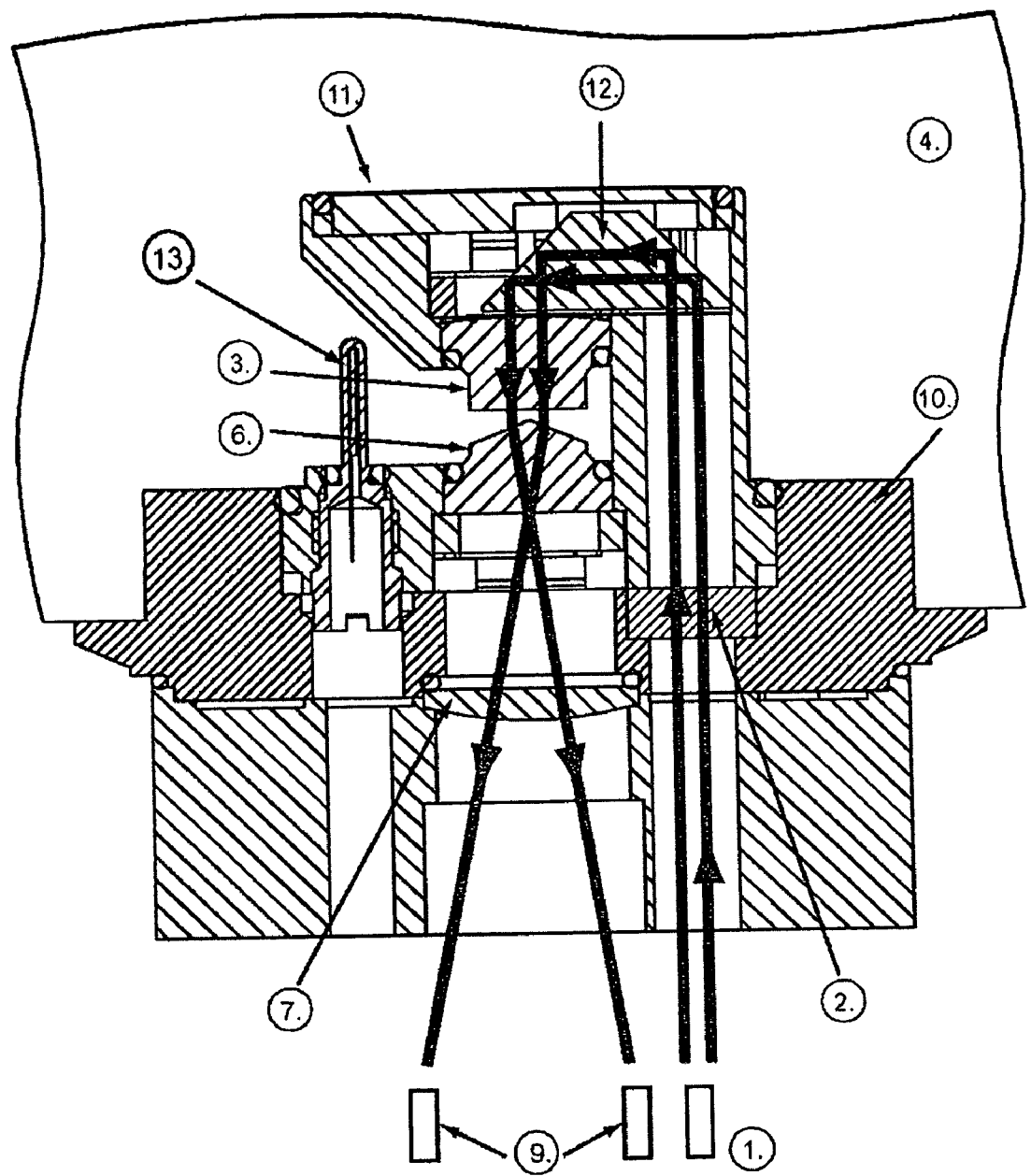
FIG. 4 depicts an embodiment in accordance with the invention with a temperature sensor.

FIG. 4 depicts the inventive transmitted light refractometer in the embodiment as in FIG. 2 and FIG. 3, and an integrated temperature detector 13, which enables precise and rapid compensation of the temperature correlation for the refractive index. The temperature detector 13 is arranged such that it is disposed a short distance from the optical measurement segment (see FIG. 4). This ensures that the measured temperature deviates minimally from the actual temperature of the medium through which the transmitted light passes. The temperature detector 13 is preferably incorporated in a free-standing thin-walled separate housing part so that the measurement medium flows around the sensor and the sensor has low heat conduction to the refractometer housing. In this manner rapid reaction of the temperature measurement to changes in the media temperatures is attained and the temperature measurement is decoupled from the housing temperature.

The temperature correlation of the optical refractive index is thus compensated in an optimal manner. The temperature detector preferably contains a Pt100 or Pt1000 resistance temperature detector. These type sensors measure very precisely across a wide temperature range.

Another advantageous embodiment of the refractometer in accordance with FIG. 2 and FIG. 3 has illumination optics unit 2 or imaging optics unit 7 integrated in the window 3 and in the measurement prism 6. The illumination and imaging lenses are ground onto the side of the window 3 or measurement prism 6 that faces away from the process. Integrating the optical components makes it possible for the refractometer to have a more compact structure.

REFERENCE LIST

1 Slit
2 Illumination optics unit
3 Window
4 Process medium
5 Measurement chamber
6 Measurement prism
7 Focusing optics unit
8 Beam
9 Detector plane
10 Process flange
11 Sensor head
12 Deflecting optics unit
13 Temperature detector

The invention claimed is:

1. A transmitted light refractometer, comprising:
    a light source on a radiation side of an immersible portion of said transmitted light refractometer which is immersible in a process liquid;
    an illumination optics unit configured for parallelizing light emitted from said light source;
    a reversing optics unit which is oriented relative to said illumination optics unit such that the reversing optics unit deflects the parallel beam into a general direction back to said radiation side of said immersible portion along a reversed light path;
    a window being disposed in said immersible portion, a surface of said window being in contact with the process liquid when said immersible portion is immersed, said surface being aligned with a first plane oriented generally perpendicular to said reversed light path;
    a measurement prism being disposed in said immersible portion including a light entry surface in contact with the process liquid which is aligned with a second plane oriented at an oblique angle with respect to said reversed light path so as to refract said light traveling along said reversed light path such that said light is redirected along a refracted light path, said measurement prism further including a light exiting surface through which said light traveling along said refracted light path exits said measurement prism and passes back to the radiation side; and
    a focusing optics unit configured to focus the light which exits said measurement prism onto a detector plane, the focusing optics unit and the detector plane being arranged on the radiation side, so that only one access to the process medium is required.

2. A transmitted light refractometer according to claim 1, wherein said reversing optics unit includes a dove prism.

3. A transmitted light refractometer according to claim 1, wherein said measurement prism includes a double prism that has two flat surfaces that are symmetrically inclined to a plane of symmetry, the plane of symmetry being perpendicular to a reference plane.

4. A transmitted light refractometer according to claim 1, further comprising a temperature detector which is arranged in the process liquid such that said temperature detector is disposed a short locational distance from the optical measurement segment.

5. A transmitted light refractometer according to claim 4, wherein said temperature detector is integrated in a separate, free-standing thin-walled housing part.

6. A transmitted light refractometer according to claim 2, wherein said measurement prism includes a double prism that has two flat surfaces that are symmetrically inclined to a plane of symmetry, the plane of symmetry being perpendicular to a reference plane.

7. A transmitted light refractometer according to claim 2, further comprising a temperature detector which is arranged in the process liquid such that said temperature detector is disposed a short locational distance from the optical measurement segment.

8. A transmitted light refractometer according to claim 3, further comprising a temperature detector which is arranged in the process liquid such that said temperature detector is disposed a short locational distance from the optical measurement segment.

9. A transmitted light refractometer according to claim 7, wherein said temperature detector is integrated in a separate, free-standing thin-walled housing part.

10. A transmitted light refractometer according to claim 8, wherein said temperature detector is integrated in a separate, free-standing thin-walled housing part.

* * * * *